(12) United States Patent
Vortman et al.

(10) Patent No.: US 11,123,575 B2
(45) Date of Patent: Sep. 21, 2021

(54) 3D CONFORMAL RADIATION THERAPY WITH REDUCED TISSUE STRESS AND IMPROVED POSITIONAL TOLERANCE

(71) Applicants: Kobi Vortman, Haifa (IL); Yoav Levy, Hinanit (IL)

(72) Inventors: Kobi Vortman, Haifa (IL); Yoav Levy, Hinanit (IL)

(73) Assignee: INSIGHTEC, LTD., Tirat Carmel (IL)

( * ) Notice: Subject to any disclaimer, the term of this patent is extended or adjusted under 35 U.S.C. 154(b) by 634 days.

(21) Appl. No.: 15/637,163

(22) Filed: Jun. 29, 2017

(65) Prior Publication Data

US 2019/0001154 A1    Jan. 3, 2019

(51) Int. Cl.
| | |
|---|---|
| *A61N 5/10* | (2006.01) |
| *A61B 5/00* | (2006.01) |
| *A61N 7/02* | (2006.01) |
| *A61B 34/10* | (2016.01) |
| *A61B 6/03* | (2006.01) |
| *A61B 6/00* | (2006.01) |
| *A61N 7/00* | (2006.01) |
| *A61B 6/12* | (2006.01) |

(52) U.S. Cl.
CPC ............ *A61N 5/1049* (2013.01); *A61B 5/489* (2013.01); *A61B 34/10* (2016.02); *A61N 5/103* (2013.01); *A61N 5/1039* (2013.01); *A61N 5/1048* (2013.01); *A61N 5/1064* (2013.01); *A61N 7/02* (2013.01); *A61B 5/4836* (2013.01); *A61B 6/03* (2013.01); *A61B 6/12* (2013.01); *A61B 6/504* (2013.01); *A61N 2005/1055* (2013.01); *A61N 2005/1087* (2013.01); *A61N 2005/1098* (2013.01); *A61N 2007/0039* (2013.01)

(58) Field of Classification Search
CPC .... A61N 5/1001; A61N 5/103; A61N 5/1031; A61N 5/1039; A61N 5/1042; A61N 5/1043; A61N 5/1044; A61N 5/1045; A61N 5/1048; A61N 5/1049
See application file for complete search history.

(56) References Cited

U.S. PATENT DOCUMENTS

2007/0016039 A1* 1/2007 Vortman ............... A61B 8/467
                                                    600/439
2008/0221382 A1   9/2008 Karshafian et al.
(Continued)

FOREIGN PATENT DOCUMENTS

EP        2343103 A1    7/2011

OTHER PUBLICATIONS

Extended European Search Report for European Application No. 18180302.4 dated Nov. 21, 2018 5 pages.

*Primary Examiner* — David P Porta
*Assistant Examiner* — Mamadou Faye
(74) *Attorney, Agent, or Firm* — Morgan, Lewis & Bockius LLP (57) ABSTRACT

An approach for enhancing radiation treatment of target tissue includes identifying a target volume of the target tissue; causing disruption of vascular tissue in a region confined to the target volume so as to define the target volume; based at least in part on the disruption of the vascular tissue, determining a radiation treatment plan having a reduced radiation dose for treating the target tissue; and exposing the target volume to the reduced radiation dose based on the radiation treatment plan.

34 Claims, 9 Drawing Sheets

(56) References Cited

U.S. PATENT DOCUMENTS

| | | | |
|---|---|---|---|
| 2012/0116221 A1* | 5/2012 | Sehgal | A61N 7/00 600/439 |
| 2014/0343421 A1 | 11/2014 | Kim et al. | |
| 2014/0378737 A1* | 12/2014 | Carpenter | G16H 50/70 600/1 |
| 2015/0196638 A1* | 7/2015 | Czamota | A61N 5/10 600/1 |

* cited by examiner

3D CONFORMAL RADIATION THERAPY WITH REDUCED TISSUE STRESS AND IMPROVED POSITIONAL TOLERANCE

FIELD OF THE INVENTION

The invention relates generally to a radiation therapy and, more particularly, to systems and methods for reducing tissue stress and improving positional tolerance when performing the radiation therapy.

BACKGROUND

Radiation therapy has been at the forefront of advances in the treatment of cancer for the past century. A minimally invasive modality that can treat disease even when the tumor is intermingled with normal tissue, it also allows flexibility in adjusting dose regimens according to the character and extent of the disease and for each patient. In practice, a radiation device (e.g., a linear accelerator or "linac") emits a beam of ionizing radiation to one or more target tumors; the ionizing radiation damages the DNA of tumor cells and thereby kills them. Despite its effectiveness, numerous challenges remain.

For example, to ensure the arrival of sufficient radiation at the target tumor for efficient treatment, high intensities are required. Use of a high-intensity beam, however, may result in collateral damage to non-target, healthy tissue (e.g., skin and/or organs) located on the radiation beam path. To avoid this undesired effect, conventional systems implement intensity-modulated radiation therapy (IMRT) that utilize a plurality of lower-intensity radiation beams converging from various angles; the beams collectively form a constructive, high-intensity focal zone at the target tumor. Accordingly, IMRT requires the radiation beams to be precisely focused onto the target location in order to avoid damage to healthy tissue surrounding the target. However, because the resolution of the radiation beams in the direction of beam propagation is limited, treatment in the direction of beam propagation may be less accurate and the surrounding healthy tissue in this direction may be unnecessarily damaged. In addition, because the human body is flexible and moves even when a patient is positioned to keep still (due to respiration, for example, or small involuntary movements), movement of the target tissue presents another challenge to radiation treatment.

Conventionally, an imaging modality, such as X-rays, computer tomography (CT) or magnetic resonance imaging (MRI), is used in conjunction with the radiation device during treatment to monitor the location of the target tissue. Often, however, it is difficult to distinguish the tumor tissue from healthy tissue in the image, particularly when they are intermingled. It thus becomes necessary to stop the treatment process and correct for any misalignment due to displacement of the target tissue or organ before treatment can be resumed. This results in significant inefficiencies in the radiation treatment process, and may cause inconvenient delays.

Accordingly, there is a need for target-identifying approaches that facilitate tracking the target region and compensating for its motion in real time during the radiation treatment.

SUMMARY

The present invention provides systems and methods for accurately labeling the target region in three dimensions (3D) by first defining a set of voxels corresponding to a target volume using any suitable imaging modality (e.g., a magnetic resonance imaging (MRI) apparatus) and then performing vascular disruption by focused ultrasound confined to the target volume. Because the target region with disrupted vascular tissue can be easily and clearly observed using a suitable imaging modality, (e.g., an MRI apparatus), a radiation device can be operated to emit radiation beams to the imaged target region for treatment. In various embodiments, the disrupted vascular tissue can be continuously imaged, and the images monitored, during treatment to ensure that the target motion is compensated for and the surrounding healthy tissue (i.e., tissue outside of the boundaries of the disrupted tissue region) is substantially not exposed to the radiation treatment (i.e., not exposed at all or to a clinically insignificant degree).

In one implementation, the vascular tissue is disrupted in a controlled and reversible manner using acoustic energy generated from focused ultrasonic pulses. A phased-array ultrasound transducer can generate a focal zone in the target region with an excellent 3D resolution (e.g., of 1-3 mm), including depth focusing (i.e., varying focal depths along a focal path in the direction of beam propagation) and lateral beam steering (i.e., beam steering in the direction perpendicular to beam propagation). The transducer may be sequentially focused and activated at a number of focal zones in close proximity to one another; this series of "sonications" may collectively cause disruption of the vascular tissue within the target region. The disruption may manifest itself in leakage of the capillaries. In addition, each focal zone may be shaped (e.g., to a focal point or toroid). Accordingly, the target region marked and sensitized by ultrasound-mediated tissue disruption may be highly accurate (e.g., having a resolution of 1-3 mm); this thereby minimizes unnecessary damage to the surrounding healthy tissue during subsequent radiation treatment. In various embodiments, microbubbles are optionally generated (e.g., acoustically) at the target region, locally injected into the target region, and/or systemically injected into the patient's brain. Application of the ultrasonic pulses to the microbubbles may results in an array of behaviors known as acoustic cavitation, which can assist in tissue disruption at the target region.

In some embodiments, disruption of the targeted vascular tissue is performed under real-time image guidance using the imaging modality. Once the disruption is complete, images of the target region having disrupted vascular tissue are compared against the 3D voxels of the target volume defined prior to the ultrasound procedure so as to verify accuracy of the marked target region. If the marked region is smaller than the defined target volume, additional sonication may be performed to disrupt the unmarked target volume. If, however, the marked region is larger than the defined target volume, the patient may rest for one or two days until the vascular tissue at the target region has regenerated and is ready to be disrupted again. Once the disrupted vascular region is verified to match the defined target volume, a radiation dose for treating the target region may be determined. In one embodiment, due to the disruption of the vascular tissue, the radiation dose can be reduced (e.g., by up to a factor of ten) to cause the same cell death rate in the target region compared with the conventional radiation dose applied to the target region without disrupted vascular tissue.

Accordingly, using ultrasound pulses (with or without assistance from microbubble cavitation) to disrupt vascular tissue at the target region may serve to accurately define the target region, enabling it to be clearly and accurately observed during radiation treatment. This advantageously allows the target tissue to be continuously tracked in real time during treatment, thereby allowing more precise application of radiation and avoiding damage to the non-target tissue. In addition, because disruption of the vascular tissue is reversible, marking the target region using vascular tissue disruption may be used to correct inaccurate target delineation after the previous disruption is reversibly eliminated (which may take up to 24 hours). Finally, the ultrasound-mediated vascular disruption may allow the radiation dose to be significantly reduced while still achieving a desired efficiency of the treatment.

Accordingly, in one aspect, the invention pertains to a method of enhancing radiation treatment of target tissue. In various embodiments, the method includes (a) identifying a target volume of the target tissue; (b) causing disruption of vascular tissue in a region confined to the target volume so as to define the target volume; (c) based at least in part on the disruption of the vascular tissue, generating and electronically storing a radiation treatment plan having a reduced radiation dose for treating the target tissue; and (d) exposing the target volume to the reduced radiation dose based on the radiation treatment plan. In one implementation, the radiation treatment plan specifies a radiation dose, a direction of an ionizing beam, and/or activation of one or more radiation generators. In addition, the method may further include generating and delivering one or more sonications of shaped acoustic energy beams to the target volume for causing the disruption of the vascular tissue. When multiple sonications are generated, each sonication delivers focused acoustic energy beams to a focal zone in the target volume, and multiple focal zones collectively cover the target volume.

The method may further include defining a center region and a peripheral region of the target volume; the intensity of the focused acoustic energy beams in the center region may be different from (e.g., larger than) the intensity of the focused acoustic energy beams in the peripheral region. In addition, the method may include identifying a radiation-sensitive region outside the target volume and defining the first and second regions of the target volume; the first region may be closer to the radiation-sensitive region than the second region to the radiation-sensitive region. In addition, the intensity of the focused acoustic energy beams in the first region may be larger than the intensity of the focused acoustic energy beams in the second region.

In some embodiments, the method includes causing cavitation of microbubbles in the target volume to disrupt the vascular tissue therein. The microbubbles may be generated by the focused acoustic energy beams and/or injected into the target volume. In various embodiments, the method includes generating a vascular disruption map of the target volume. The vascular disruption map may be generated, for example, based at least in part on MRI perfusion imaging, MRI contrast imaging, a planning map of vascular disruption, and/or an acoustic response of the target volume during disruption of the vascular tissue. In addition, the method may include comparing a target volume in the vascular disruption map to the 3D set of voxels associated with the target volume acquired in step (a), and the target volume is exposed to the reduced radiation dose only if the target volume in the vascular disruption map matches the target volume acquired in step (a). In one embodiment, the vascular disruption map includes disruption levels of tissue in the target volume, and the radiation treatment plan is determined based on the disruption levels.

The method may further include continuously tracking the target volume defined by the disruption of vascular tissue during step (d) and adjusting the radiation treatment plan to compensate for movement of the target volume. In one implementation, the target volume of the target tissue is identified based on imaging data. In some embodiments, the method includes generating a sonication plan specifying an intensity, a phase, a frequency associated with an ultrasound transducer element, a sonication grid density and/or a time interval between consecutive series of sonications for causing the disruption of the vascular tissue. The sonication grid density may be determined based on the imaging data and/or an acoustic signal from the target volume.

In another aspect, the invention relates to a system for enhancing radiation treatment of target tissue. In various embodiments, the system includes an imaging device for acquiring a 3D set of voxels corresponding to a target volume of the target tissue; an ultrasound transducer for generating and delivering one or more sonications of focused beams confined to the target volume for causing disruption of vascular tissue therein so as to define the target volume; a controller configured for determining, based at least in part on the disruption of the vascular tissue, a radiation treatment plan having a reduced radiation dose for treating the target tissue; and a radiation device for transmitting the reduced radiation dose to the target volume. In one implementation, the radiation treatment plan specifies a radiation dose, a direction of an ionizing beam, and/or activation of one or more radiation generators. In addition, when multiple sonications are generated; each delivers focused acoustic energy beams to a focal zone in the target volume, and multiple focal zones collectively cover the target volume. One or more of the sonications may cause cavitation of microbubbles in the target volume. In some embodiments, the system further includes an administration device for injecting microbubbles into the target volume.

The controller may be configured to define a center region and a peripheral region of the target volume; the intensity of the focused acoustic energy beams in the center region being may be different from (e.g., larger than) the intensity of the focused acoustic energy beams in the peripheral region. In various embodiments, the controller is further configured to identify a radiation-sensitive region outside the target volume and define the first and second regions of the target volume; the first region is closer to the radiation-sensitive region than the second region to the radiation-sensitive region. In addition, the intensity of the focused acoustic energy beams in the first region is larger than the intensity of the focused acoustic energy beams in the second region.

The controller may be configured to generate a vascular disruption map of the target volume. For example, the vascular disruption map may be generated based on MRI perfusion imaging, MRI contrast imaging, a planning map of vascular disruption, and/or an acoustic response of the target volume during disruption of the vascular tissue. In addition, the controller may be further configured to compare a target volume in the vascular disruption map to the 3D set of voxels associated with the target volume acquired in step (a); the target volume may be exposed to the reduced radiation dose only if the target volume in the vascular disruption map matches the target volume acquired in step (a). In some embodiments, the vascular disruption map includes disruption levels of tissue in the target volume. The controller may then be configured to determine the radiation treatment plan based on the disruption levels.

In various embodiments, during step (d), the imaging device acquires multiple images for continuously tracking the target volume defined by the disruption of vascular tissue; and the controller is further configured to adjust the radiation treatment plan to compensate for movement of the target volume. In one embodiment, the controller is configured to generate a sonication plan specifying an intensity, a phase, and/or a frequency associated with an ultrasound transducer element so as to generate and deliver the sonication(s) of focused beams. In addition, the controller may be configured to generate a sonication plan specifying a sonication grid density and/or a time interval between consecutive series of sonications; and based on the sonication plan, cause the ultrasound transducer to generate multiple sonications for causing the disruption of the vascular tissue. In some embodiments, the controller is configured to determine the sonication grid density based on the imaging data and/or an acoustic signal from the target volume.

As used herein, the term "substantially" means ±10%, and in some embodiments, ±5%. In addition, the term "element" means either an individual transducer in an array or an independently drivable portion of a single transducer, and the terms "beam," "energy beam," or "acoustic energy beam" refer generally to the sum of the waves emitted by the various transmitting elements of a focused ultrasound system. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1A:
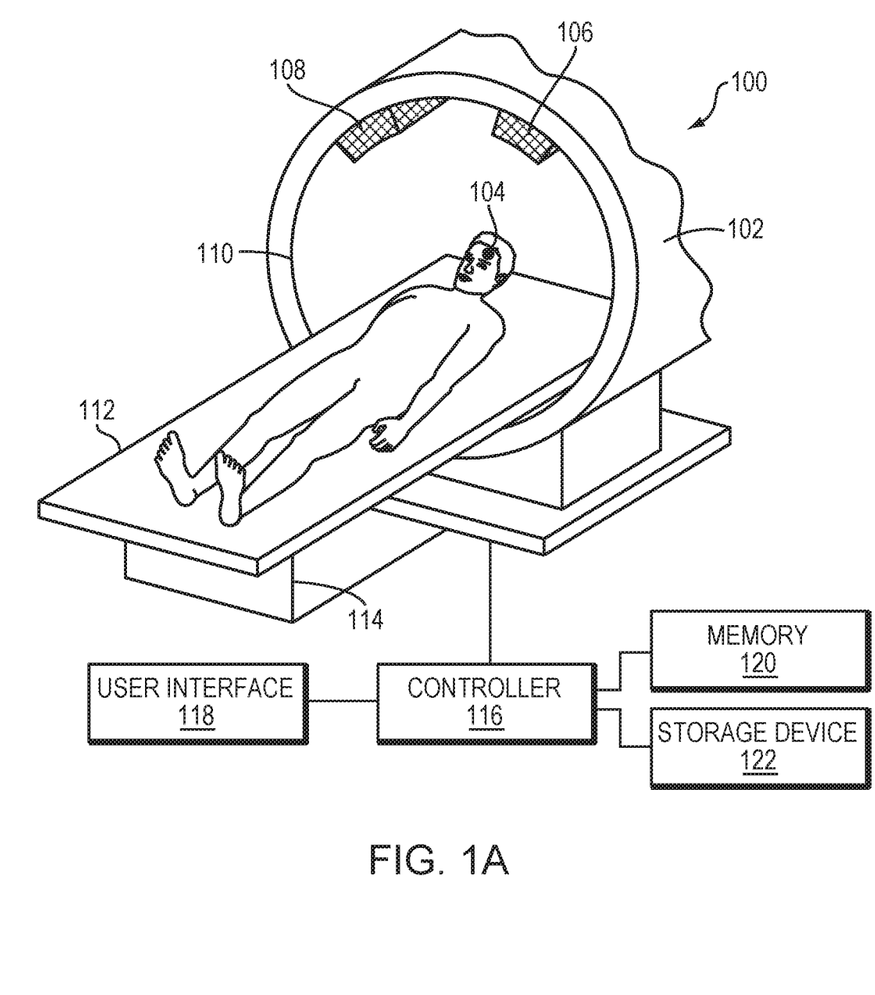
FIG. 1A illustrates an exemplary radiation treatment system in accordance with some embodiments of the present invention.

FIG. 1A illustrates an exemplary radiation treatment system 100 in accordance with embodiments of the present invention. The radiation treatment device 100 may include a treatment apparatus 102 which, when activated, emits one or more ionizing beams directed at a target region 104. For example, the treatment apparatus 102 may include two x-ray generators 106, 108, each generating an ionizing beam; the two ionizing beams collectively form a constructive, high-intensity focusing beam having sufficient energy to cause the target region 104 to become necrotic. The treatment apparatus 102 may include, for example, a linear accelerator, a synchrocyclotron or preferably an x-ray linear accelerator. Such treatment apparatus 102 are readily available commercially.

The radiation treatment device 100 may also include a motion-compensation device for adjusting the relative positions of the treatment apparatus 102 and the patient such that the ionizing beam(s) can be continuously focused on the target region during treatment even when the target region moves. In one embodiment, the motion-compensation device includes a gantry 110 and a moveable operating table 112 with a tilting top 114. In another embodiment, motion-compensation device includes a processor controllable robotic arm mechanism (not shown); the robotic arm mechanism permits the treatment apparatus 102 to be moved freely about the patient's body including up, down, longitudinally along or laterally along the body of the patient. In either case, the motion-compensation device allows positions of the treatment apparatus 102 and the patient to be altered with six degrees of freedom.

The radiation treatment system 100 may further include a radiation source controller 116 for regulating timing for discharges of ionizing beam(s) from the treatment apparatus 102 towards the patient. In addition, the radiation source controller 116 may be coupled to a user interface 118. The user interface 118 may be integrated with the radiation source controller 116, and will generally include a user workstation for initiating activation of the treatment apparatus 102 and controlling timing of such activation. In various embodiments, the radiation treatment system 100 further includes memory 120 and one or more non-volatile mass storage devices 122 (such as one or more hard disks and/or optical storage units) for storing a radiation treatment plan as further described below.

Figure 1B:
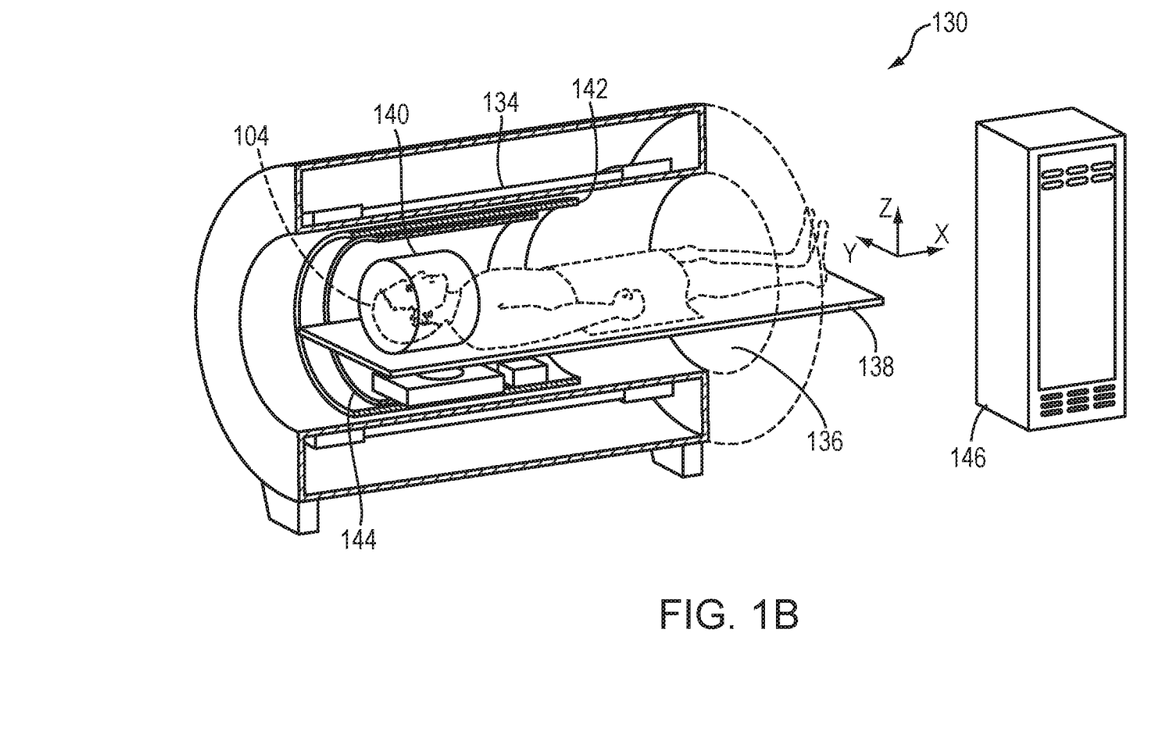
FIG. 1B illustrates an exemplary imaging system implementing an MRI apparatus in accordance with some embodiments of the present invention.

To accurately treat the target region without damaging its surrounding tissue, it is necessary to determine the location of the target region 104 with high precision during treatment. The target, however, may move due to, for example, breathing of the patient. Therefore, it is desirable to provide an approach that allows continuous tracking of a moving target and subsequent compensation for movements of the target. Referring to FIG. 1B, in various embodiments, prior to the radiation treatment, an imager 130, such as an MRI device, a computer tomography (CT) device, a positron emission tomography (PET) device, a single-photon emission computed tomography (SPECT) device, or an ultrasonography device, is employed to determine information (e.g., a location, a size and/or a shape) characterizing the target region and/or the healthy tissue surrounding the target region. FIG. 1B illustrates an exemplary MRI apparatus. The MRI apparatus may include a cylindrical electromagnet 134, which generates the requisite static magnetic field within a bore 136 of the electromagnet 134. Prior to or during the medical procedures, a patient is placed inside the bore 136 on a movable support table 138. The target region 104 may be positioned within an imaging region 140 wherein the electromagnet 134 generates a substantially homogeneous field. A set of cylindrical magnetic field gradient coils 142 may also be provided within the bore 136 and surrounding the patient. The gradient coils 142 generate magnetic field gradients of predetermined magnitudes, at predetermined times, and in three mutually orthogonal directions. With the field gradients, different spatial locations can be associated with different proton precession frequencies, thereby giving an MR image its spatial resolution. An RF transmitter coil 144 surrounding the imaging region 140 emits RF pulses into the imaging region 140 to cause the patient's tissues to emit magnetic-resonance (MR) response signals. Raw MR response signals are sensed by the RF coil 144 and passed to an MR controller 146 that then computes an MR image, which may be displayed to the user. Alternatively, separate MR transmitter and receiver coils may be used.

The MRI controller 146 may control the pulse sequence, i.e., the relative timing and strengths of the magnetic field gradients, the RF excitation pulses and the response detection periods. The MR response signals are amplified, conditioned, and digitized into raw data using a conventional image-reconstruction system, and further transformed into arrays of image data by methods known to those of ordinary skill in the art. Based on the image data, the information characterizing tissue types in the target region 104 and/or the healthy tissue surrounding the target region is identified. For example, the information may include a 3D set of voxels corresponding to a target volume including the target tissue and a margin of the target tissue. The image-processing system may be part of the MRI controller 146, or may be a separate device (e.g., a general-purpose computer containing image reconstruction and processing software) in communication with the MRI controller 146.

Figure 1C:
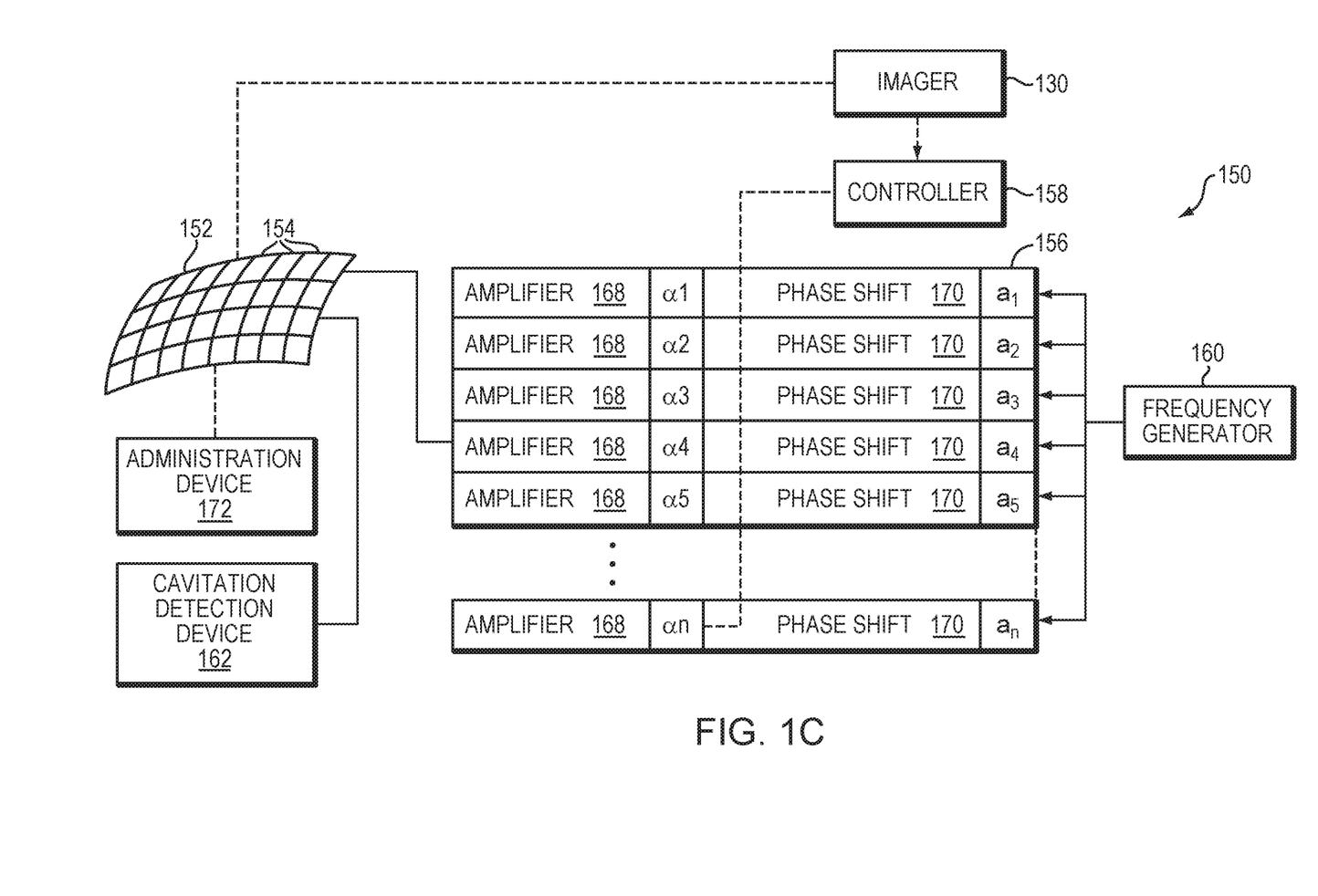
FIG. 1C illustrates an exemplary ultrasound transducer array in accordance with some embodiments of the present invention.

In various embodiments, vascular tissue in the determined target volume is then disrupted using an ultrasound system. FIG. 1C illustrates an exemplary ultrasound system 150 for generating and delivering a focused acoustic energy beam to the target region 104 for disrupting the vascular tissue therein. In various embodiments, the system 150 includes a phased array 152 of transducer elements 154, a beamformer 156 driving the phased array 152, a controller 158 in communication with the beamformer 156, and a frequency generator 160 providing an input electronic signal to the beamformer 156. The controller 158 may be integrated with or separate from the radiation source controller 116.

The array 152 may have a curved (e.g., spherical or parabolic) shape suitable for placing it on the surface of the patient's body, or may include one or more planar or otherwise shaped sections. Its dimensions may vary between millimeters and tens of centimeters. The transducer elements 154 of the array 152 may be piezoelectric ceramic elements or silicon-device based elements, and may be mounted in any material suitable for damping the mechanical coupling (crosstalk) between the elements 154. Piezo-composite materials, or generally any materials (e.g., silicon devices) capable of converting electrical energy to acoustic energy, may also be used. To assure maximum power transfer to the transducer elements 154 and minimal reflections, the elements 154 may be configured for a specific (i.e., matching) electrical impedance.

The transducer array 152 is coupled to the beamformer 156, which drives the individual transducer elements 154 so that they collectively produce a focused ultrasonic beam or field. For n transducer elements, the beamformer 156 may contain n driver circuits, each including or consisting of an amplifier 168 and a phase delay circuit 170; each drive circuit drives one of the transducer elements 154. The beamformer 156 receives a radiofrequency (RF) input signal, typically in the range from 0.1 MHz to 10 MHz, from the frequency generator 160, which may, for example, be a Model DS345 generator available from Stanford Research Systems. The input signal may be split into n channels for the n amplifiers 168 and delay circuits 180 of the beamformer 156. In some embodiments, the frequency generator 160 is integrated with the beamformer 156. The radiofrequency generator 160 and the beamformer 156 are configured to drive the individual transducer elements 154 of the transducer array 152 at the same frequency, but at different phases and/or different amplitudes.

The amplification or attenuation factors $\alpha_1$-$\alpha_n$ and the phase shifts $\alpha_1$-$\alpha_n$ imposed by the beamformer 156 serve to transmit and focus ultrasonic energy onto the target region, and account for wave distortions induced in the tissue located between the transducer elements 154 and the target region. The amplification factors and phase shifts are computed using the controller 158, which may provide the computational functions through software, hardware, firmware, hardwiring, or any combination thereof. For example, the controller 158 may utilize a general-purpose or special-purpose digital data processor programmed with software in a conventional manner, and without undue experimentation, in order to determine the phase shifts and amplification factors necessary to obtain a desired focus or any other desired spatial field patterns at the target region 104. In certain embodiments, the computation is based on detailed information about the characteristics (e.g., structure, thickness, density, etc.) of the tissue located between the transducer element 154 and their effects on propagation of acoustic energy. Such information may be obtained from the imager 130. Image acquisition may be three-dimensional or, alternatively, the imager 130 may provide a set of two-dimensional images suitable for reconstructing a three-dimensional image of the target region and/or its surrounding region. Image-manipulation functionality may be implemented in the imager 130, in the controller 158, or in a separate device.

Figure 2:
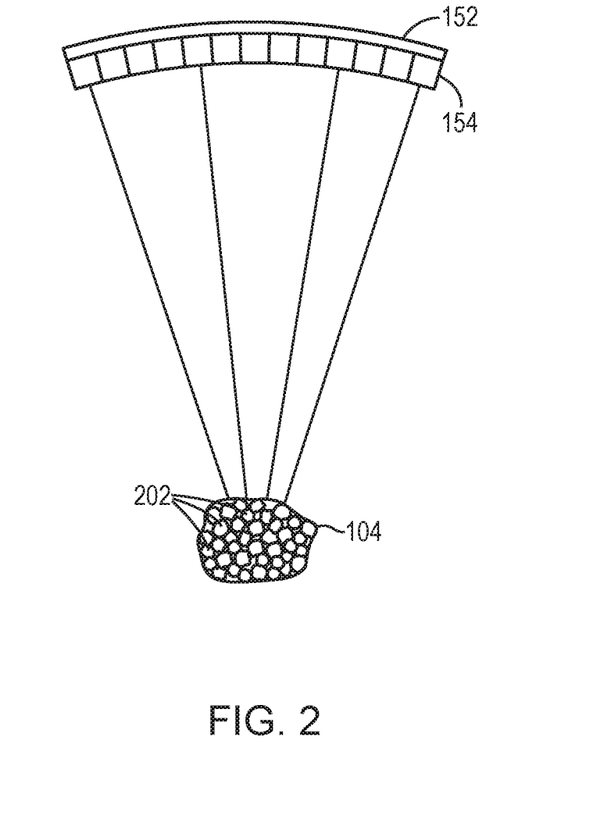
FIG. 2 depicts one or more focal zones generated by acoustic energy beams in the target region in accordance with various embodiments of the present invention.

Referring to FIG. 2, in various embodiments, after the 3D voxel set of the target volume 104 is identified using the imager 130, a sonication plan, including ultrasound parameters (such as intensities, phases, and/or frequencies associated with the transducer elements) and a 3D target definition, is determined and stored, and the transducer array 102 is activated based on the stored sonication plan so as to generate a focus zone 202 in the target volume 104 as specified in the plan. Generally, the size of the target volume 104 is larger than that of the focal zone 202. Thus, in one embodiment, the sonication plan further includes a time interval between consecutive series of sonications and/or a sonication grid density defining a successive series of focal zones and spacing therebetween; the transducer array 102 is sequentially activated based on the sonication plan to generate a number of focal zones 202 in the target volume for disrupting the vascular tissue therein. In some embodiments, the tissue-disruption procedure is monitored by the imager 130 in real-time until the focal zones generated from the series of sonications collectively cover the target volume and cause disruption of the vascular tissue therein. Because the focused ultrasound has an excellent volumetric resolution (e.g., of 1-3 mm), marking the boundaries of the target volume 104 by disrupted vascular tissue can have high accuracy. In addition, the vascular disruption may offer clear imaging of the target region 104 during the radiation treatment. Finally, because the vascular disruption is "tattooed" into the anatomic tissue and thereby moves therewith, this allows target movement to be easily tracked and compensated for, since the ionizing beams are directed only to the tattooed region in order to ensure treatment effectiveness and safety.

Figure 3:
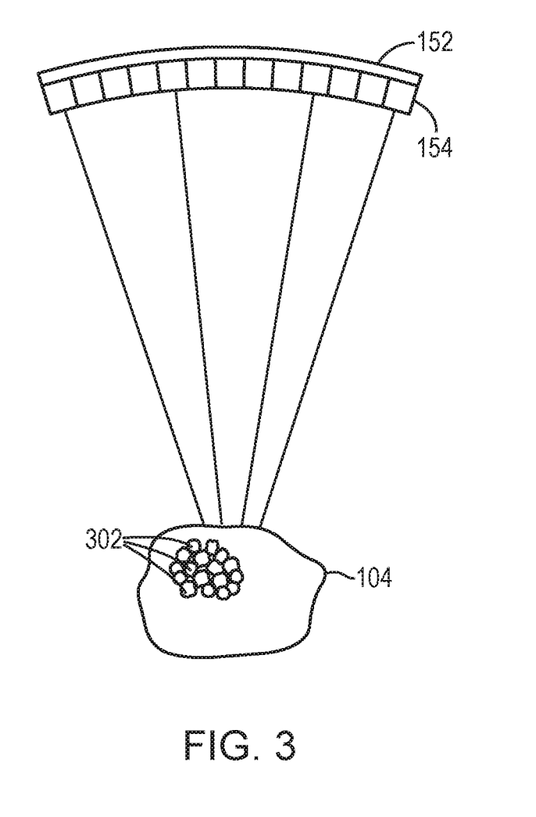
FIG. 3 depicts microbubbles generated and/or injected in the target region in accordance with some embodiments of the present invention.

Referring to FIG. 3, in various embodiments, the ultrasonic energy emitted by the transducer elements 154 may be above a threshold and thereby cause generation of a small cloud of gas bubbles (or "microbubbles") 302 in the liquid and/or plasma contained in the target region 104. The microbubbles 302 can be formed due to the negative pressure produced by the propagating ultrasonic waves or pulses, when the heated liquid ruptures and is filled with gas/vapor, or when a mild acoustic field is applied on tissue containing cavitation nuclei. At a relatively low acoustic power (e.g., 1-2 Watts above the microbubble-generation threshold), however, the generated microbubbles 302 tend to undergo oscillation with compression and rarefaction that are equal in magnitude and thus the microbubbles generally remain unruptured (i.e., a "stable cavitation" or "streaming cavitation"). At a higher acoustic power (e.g., more than 10 Watts above the microbubble-generation threshold), the generated microbubbles 302 undergo rarefaction that is greater than compression, which may cause inertial cavitation of the microbubbles in which the microbubbles in the liquid rapidly implode. The microbubble cavitation, in turn, may result in transient disruption of the vascular tissue in the targeted region 104.

Referring again to FIG. 1C, in some embodiments, an administration device 172 is employed to inject microbubbles into the target region 104 to assist disruption of the vascular tissue. The microbubbles may be introduced in the form of liquid droplets that subsequently vaporize, as gas-filled bubbles, or entrained with another suitable substance, such as a conventional ultrasound contrast agent. The injected microbubbles may themselves create or facilitate the creation of additional microbubbles. Therefore, the actual disrupting effect on the vascular tissue may result from a combination of the injected microbubbles and microbubbles additionally created in the tissue. Accordingly, in one embodiment, the sonication plan is determined based on the quantity of microbubbles predicted to be present in the target region. Prediction of the microbubbles presence may be performed based on the ultrasound parameters (e.g., intensities, locations of the focal zones, etc.) and/or microbubble characteristics (e.g., a size, a concentration, or an administration profile, i.e., a rate of injection, which may be variable, over time). In another embodiment, the sonication plan may be modified based on an acoustic signal from the microbubbles detected using the transducer array 152 and/or cavitation detection device 162. The administration device 172 may be any suitable apparatus for delivering a suspension of microbubbles into the patient's bloodstream, and can take the form of, e.g., a manual or automated syringe, an intravenous administration bag and needle set, a peristaltic pump, etc.

Figure 4A:
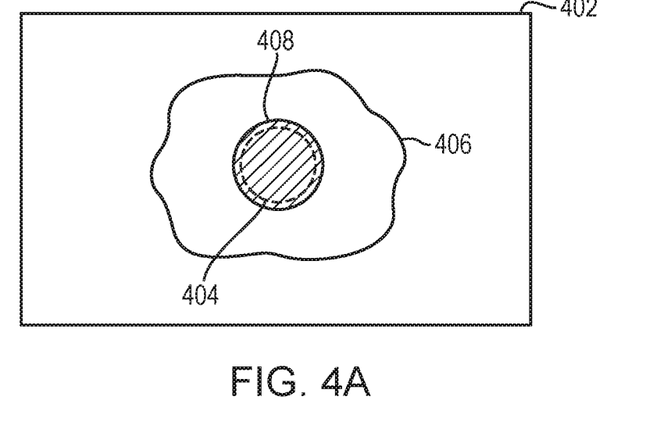
FIGS. 4A-4C depict various vascular disruption maps in accordance with some embodiments of the present invention.
Figure 4B:
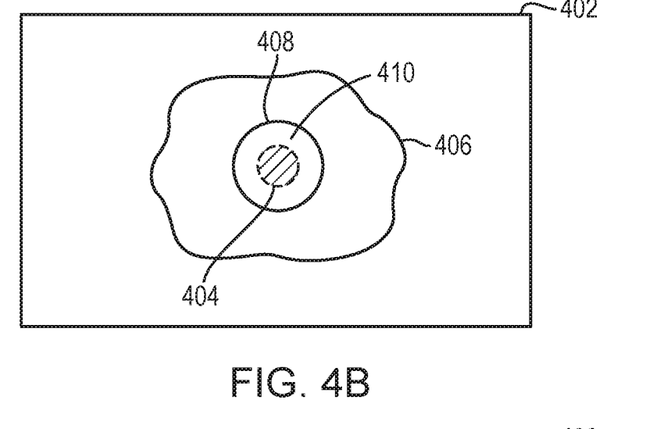
Figure 4C:
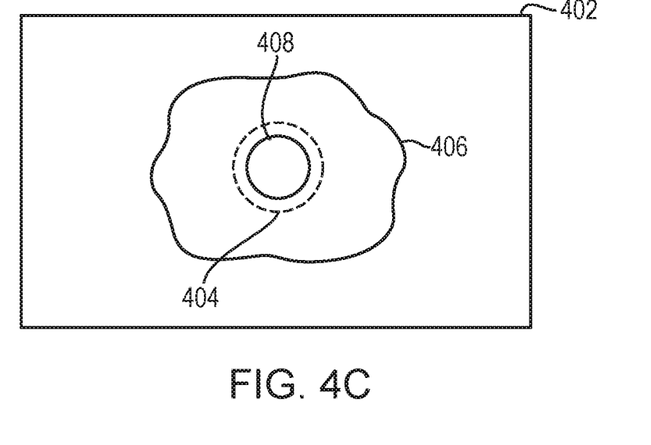

Referring to FIGS. 4A-4C, in various embodiments, after performing the ultrasound-mediated tissue disruption and prior to applying the radiation beams, an image or a "map" 402 of the target region having disrupted vascular tissue 404 and/or the surrounding healthy tissue 406 is created as described below. This map is then compared against the 3D voxel set of the target volume acquired prior to the ultrasonic procedure in order to verify accuracy of the marked target region. As depicted in FIG. 4A, if the tissue-disruption marked region 404 in the vascular disruption map 402 substantially (e.g., within 1%, 5% or 10%) matches the 3D target volume 408, the radiation device 100 may be activated to start the treatment. As depicted in FIG. 4B, if the marked region 404 is smaller than the target volume 408, additional sonication is performed in order to disrupt the unmarked target volume 410; the procedure of ultrasound-mediated tissue disruption may be continued until a substantial match between the tissue-disruption marked region 404 and target volume 408 is achieved. As depicted in FIG. 4C, in some embodiments, the marked region 404 is larger than the 3D target volume 408, the patient is required to rest for one or two days until the vascular tissue at the target region 104 is regenerated and ready for being disrupted again.

The map 402 of the vascular disrupted target region may be acquired using MRI techniques. For example, because of the vascular disruption, the perfusion rate in the target region having vascular disruption may be higher than that in the non-target region having no (or very limited) vascular disruption; this difference in perfusion may be detected and mapped using MRI-based perfusion measurements with or without administration of an MRI contrast agent. For example, dynamic susceptibility contrast MR perfusion and dynamic contrast enhanced MR perfusion may require use of a contrast agent while arterial spin labelling MR perfusion does not require the contrast agent. In some embodiments, after the vascular disruption, an MRI contrast agent is injected into the target region 104 using, for example, the administration device 172. Because of the vascular disruption, the permeability of the MRI contrast agent in the target region 104 is temporarily increased; this then results in a contrast change in the image. Accordingly, the contrast pattern can be used to estimate the size, shape and/or location of the vascular disruption. In various embodiments, various sizes (e.g., from 400 Dalton to 4,000,000 Dalton) of the MRI contrast agent are created (e.g., by combining a contrast solution with particles of various molecular sizes) and injected into the target region 104 to evaluate the disruption level of the vascular tissue. Generally, the disruption level correlates to the size of molecules capable of entering and/or diffusing in the disrupted vascular tissue. Accordingly, by selecting and injecting into the target region 104 separately resolvable MRI contrast agents having different sizes, the map may indicate various disruption levels of vascular tissue, each level indicating a specific maximal size of molecules capable of entering and diffusing in the target tissue.

Additionally or alternatively, the map 402 of the disrupted target region may be established based at least in part on a localized acoustic response (e.g., an instantaneous acoustic response level and/or a spectral distribution of the acoustic response) from the microbubbles at the target region 104 during vascular disruption; the acoustic response may be detected using a cavitation detection device 162 (shown in FIG. 1C) and/or the ultrasound transducer array 102. Generally, the size and/or degree of the vascular disruption correlates to the amount of induced microbubble cavitation in the target region 104. Thus, by detecting the acoustic response emanating from the microbubbles localized at the target region 104, the degree of tissue disruption can be inferred, and with sufficient detection resolution, a map 402 can be generated.

Additionally or alternatively, the vascular disruption map 402 may be created based on vascular disruption planning. Generally, the size and/or degree of the vascular disruption correlates with the microbubble concentration and/or the delivered acoustic power (or power density) and energy in the target region 104. Thus, by synchronizing the distribution of the acoustic power with microbubble administration, a temporal and/or cumulative expected cavitation or other acoustic effect during the sonication can be calculated and/or simulated. A planning map indicating a degree of vascular tissue disruption can then be inferred from the calculation and/or simulation.

Figure 5:
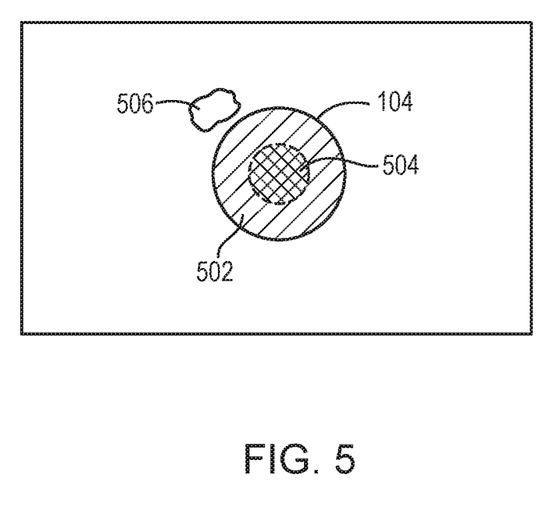
FIG. 5 illustrates the target region and non-target region in accordance with some embodiments of the present invention.

The intensity of the ultrasound beams may be varied when disrupting the vascular tissue in the target region 104. Referring to FIG. 5, in some embodiments, the ultrasound intensity is adjusted based on the relative positions of the generated focal zone and the target region 104. For example, the intensity of the beams focusing at the peripheral region 502 of the target may be smaller than that of the beams focusing at the center region 504 of the target. This way, when the focused ultrasound beam is at the peripheral region 502 of the target, only the vascular tissue is disrupted for marking purposes, whereas when the focused ultrasound beam is at the center region 504 of the target, the vascular tissue as well as the tumor tissue may be ablated for treatment purposes. As used herein, the "center region" may include the entire target region 104 except the regions forming the boundaries. Alternatively, the "center region" may include only a fraction of the radial extent—e.g., 10%, 20%, 50%, etc. The "peripheral region" typically includes all of the target region outside the center region 504. In various embodiments, the ultrasound intensity is adjusted based on the relative positions of the focal zone in the target region 104 and a radiation-sensitive non-target region 506 (i.e., a region outside the target region that can tolerate only low radiation energy levels). The intensity of the ultrasound beams may be increased as the distance between the focal zone and the radiation-sensitive non-target region 506 decreases. In this way, a higher percentage of the target tissue near the radiation-sensitive non-target region 506 may be disrupted by the ultrasound beams and, consequently, a lower dose of radiation is required for treatment. This approach avoids (or at least reduces) the risk of damaging the radiation-sensitive non-target region 506 located near the target region 104.

Once the ultrasound-mediated tissue disruption region is verified to match the defined target volume, a radiation treatment plan including, for example, a radiation dose and/or other parameters (e.g., directions, activation of various radiation generators, etc.) for treating the target can be computationally generated. In one embodiment, a computational model is used to create the radiation treatment plan. The computational model may be implemented in the radiation source controller 116 or in another computational entity (including a suitable processor and memory) within, or in communication with, the radiation treatment device 100, and may utilize information acquired using the imager 130. For example, as described above, the MRI imaging may be utilized to evaluate the disruption level of the vascular tissue. The relationship between the tissue disruption level and the radiation dose for efficient treatment may be established empirically and/or by simulation and may be included in the computational model. In addition, the MRI imaging and/or CT imaging may be used to extract anatomical characteristics (such as the type, thickness, or density) of intervening tissue located on the ionizing beam paths between the radiation treatment device 100 and target region 104. Different tissue characteristics may have different responses to the ionizing beams. For example, while soft tissue may absorb some energy, calcium in bones may absorb more. Therefore, in some embodiments, the anatomic characteristics and corresponding radiation response of the intervening tissue are also included in the computational model.

Figure 6:
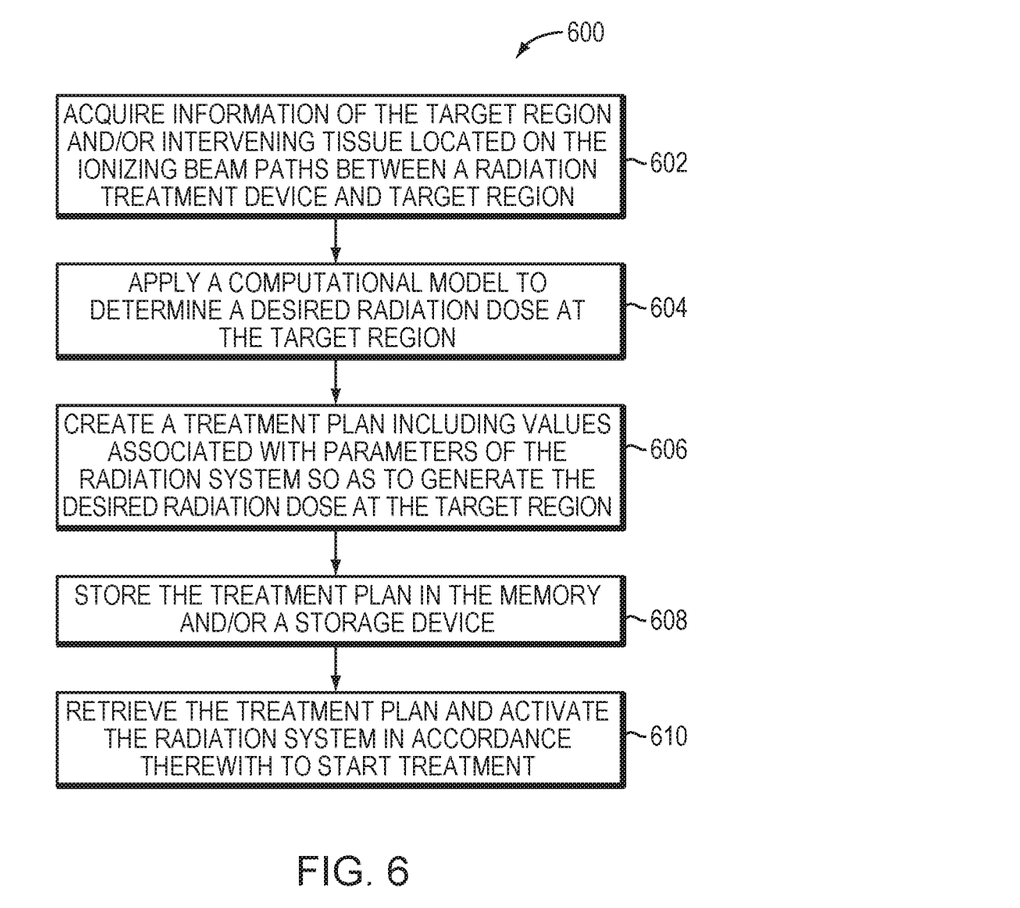
FIG. 6 is a flow chart illustrating an approach of generating a radiation treatment plan in accordance with various embodiments of the present invention.

FIG. 6 illustrates a representative approach 600 for generating the radiation treatment plan using a computational model in accordance with various embodiments. In a first step 602, an imager 130 is utilized to acquire information (e.g., a location or a disruption level) of tissue in the target region 104 as well as anatomical characteristics of the intervening tissue. In a second step 604, based on the target tissue information, the radiation source controller 116 may apply the computational model to determine a desired radiation dose at the target region. In a third step 606, the computational model may create a treatment plan including values associated with parameters of the radiation system 100 (e.g., intensities and/or directions of the ionizing beams emitted from the x-ray generators 106, 108 and/or activation time of the generators 106, 108) so as to generate the desired radiation dose at the target region. The treatment plan may then be stored in the memory 120 and/or storage device 122 (in a fourth step 608). During radiation treatment, the radiation source controller 116 may retrieve the treatment plan and activate the radiation system in accordance therewith to generate ionizing radiation beams having a desired dose at the target region 104 (in a fifth step 610).

In some embodiments, the ultrasonic disruption of the target tissue advantageously allows the radiation dose to be reduced while still achieving treatment efficiency. For example, the radiation dose for treating the target region 104 having disrupted vascular tissue may be reduced (e.g., by up to a factor of ten) to achieve the same cell death rate compared to treatment using a higher radiation dose for treating a target region having undisrupted vascular tissue. As used herein, a reduced radiation dose means that the radiation dose is at least 50% smaller than that applied in conventional radiation therapy for similar targets and intervening anatomy, and in some embodiments, it may be up to ten times smaller.

In various embodiments, during the radiation treatment, the imager 130 continuously monitors the location of the target region 104 that has been marked with the disrupted vascular tissue in real time. Based thereon, the radiation source controller 116 may adjust the parameters associated with the treatment apparatus 102 in the radiation treatment plan so as to compensate for the movement and/or swelling of the target region 104, thereby ensuring treatment efficiency and avoiding damaging the non-target tissue.

Figure 7:
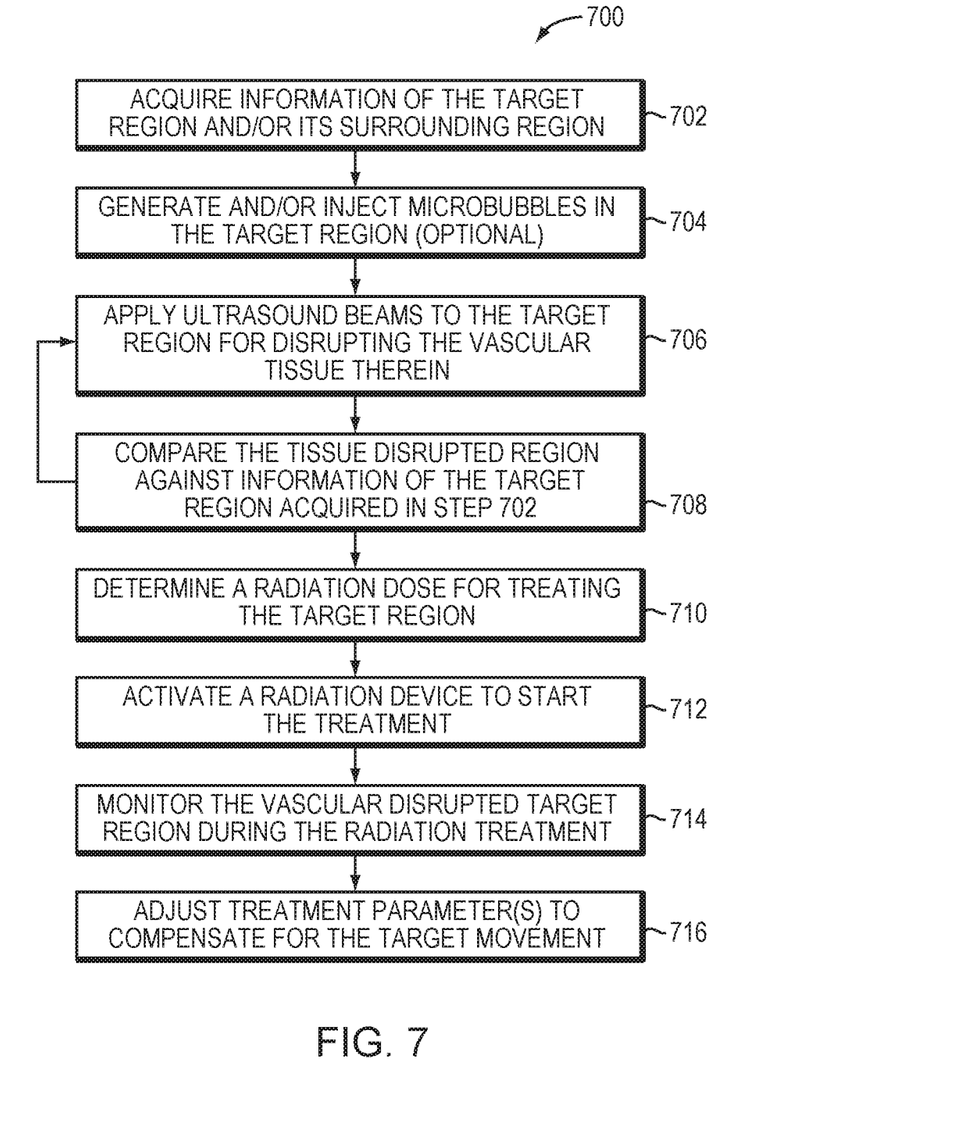
FIG. 7 is a flow chart illustrating an approach of using ultrasound sonication to assist and/or enhance radiation treatment in accordance with some embodiments of the present invention.

FIG. 7 illustrates a representative approach 700 using ultrasound sonication to assist and/or enhance radiation treatment by temporarily disrupting vascular tissue in the target region 104 in a controlled and reversible manner. In a first step 702, an imager (e.g., an MRI device) is utilized to acquire information (such as location, size, or shape) of the target region 104 and/or its surrounding region prior to applying the ultrasound sonication; the target information may include a 3D set of voxels corresponding to the target region 104. Optionally, in a second step 704, microbubbles may be injected and/or generated in the target region for assisting disruption of the vascular tissue. In a third step 706, based on the defined target information, focused ultrasound beams are applied to the target region 104 so as to disrupt the vascular tissue therein. The vascular tissue disruption may also result from microbubble cavitation if the microbubbles are present in the target region 104. The tissue disrupted region may then be compared against the target volume acquired in step 702 to verify the match therebetween (in a fourth step 608). Steps 706 and 708 may be iteratively performed until the vascular disrupted region substantially matches the defined target volume. In some embodiments, a vascular disruption map of the target region 104 is optionally created and utilized for comparing with the defined target volume. In a fifth step 710, a radiation dose for treating the target region may then be determined. Finally, in a sixth step 712, the radiation device is activated to start the treatment. In various embodiments, the vascular disrupted target region is continuously monitored using the imager 130 during the radiation treatment (in a seventh step 714). Based thereon, parameters of the radiation device may be adjusted to compensate for the target movement and/or swelling (in an eighth step 716).

In general, functionality for generating the radiation treatment plan and/or sonication plan using the radiation source controller 116 and/or the ultrasound controller 158 as described above may be structured in one or more modules implemented in hardware, software, or a combination of both. For embodiments in which the functions are provided as one or more software programs, the programs may be written in any of a number of high level languages such as FORTRAN, PASCAL, JAVA, C, C++, C #, BASIC, various scripting languages, and/or HTML. Additionally, the software can be implemented in an assembly language directed to the microprocessor resident on a target computer; for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of enhancing radiation treatment of target tissue, the method comprising:
    (a) identifying a target volume of the target tissue;
    (b) generating and delivering at least one sonication of shaped acoustic energy beams confined to the target volume for causing disruption of vascular tissue therein so as to define the target volume;
    (c) continuously monitoring the disruption of vascular tissue in real-time during step (b);
    (d) based at least in part on the monitored disruption of the vascular tissue, adjusting a sonication parameter value associated with the acoustic energy beams;
    (e) based at least in part on the disruption of the vascular tissue, generating and electronically storing a radiation treatment plan having a reduced radiation dose for treating the target tissue; and
    (f) exposing the target volume to the reduced radiation dose based on the radiation treatment plan,
    wherein the target volume is exposed to the reduced radiation dose only if the monitored disruption of the vascular tissue substantially matches a desired vascular disruption map.

2. The method of claim 1, wherein a plurality of sonications are generated, each delivering focused acoustic energy beams to a focal zone in the target volume, and a plurality of the focal zones collectively covers the target volume.

3. The method of claim 2, further comprising defining a center region and a peripheral region of the target volume, wherein a first intensity of the focused acoustic energy beams in the center region is different from a second intensity of the focused acoustic energy beams in the peripheral region.

4. The method of claim 3, wherein the first intensity is larger than the second intensity.

5. The method of claim 2, further comprising:
    identifying a radiation-sensitive region outside the target volume; and
    defining a first region and a second region of the target volume, the first region being closer to the radiation-sensitive region than the second region to the radiation-sensitive region,
    wherein a first intensity of the focused acoustic energy beams in the first region is larger than a second intensity of the focused acoustic energy beams in the second region.

6. The method of claim 1, further comprising causing cavitation of microbubbles in the target volume to disrupt the vascular tissue therein.

7. The method of claim 6, wherein the microbubbles are locally or systemically injected into the target volume.

8. The method of claim 6, wherein the microbubbles are generated by the focused acoustic energy beams.

9. The method of claim 1, wherein the vascular disruption map is generated based at least in part on at least one of MRI perfusion imaging, MRI contrast imaging, a planning map of vascular disruption, or an acoustic response of the target volume during disruption of the vascular tissue.

10. A method enhancing radiation treatment of target tissue, the method comprising;
    (a) identifying a target volume of the target tissue;
    (b) causing disruption of vascular tissue in a region confined to the target volume so as to define the target volume;
    (c) generating a vascular disruption map of the target volume;
    (d) comparing a target volume in the vascular disruption map to a 3D set of voxels associated with the target volume identified in step (a);
    (e) based at least in part on the disruption of the vascular tissue, generating and electronically storing a radiation treatment plan having a reduced radiation dose for treating the target tissue; and
    (f) exposing the target volume to the reduced radiation dose based on the radiation treatment plan
    wherein the target volume is exposed to the reduced radiation dose only if the target volume in the vascular disruption map substantially matches the target volume acquired in step (a).

11. The method of claim 1, wherein the vascular disruption map includes disruption levels of tissue in the target volume.

12. The method of claim 11, wherein the radiation treatment plan is determined based on the disruption levels.

13. The method of claim 1, further comprising:
continuously tracking the target volume defined by the disruption of vascular tissue during step (d); and
adjusting the radiation treatment plan to compensate for movement of the target volume.

14. The method of claim 1, wherein the target volume of the target tissue is identified based on imaging data.

15. The method of claim 14, further comprising generating a sonication plan comprising at least one of an intensity, a phase, a frequency associated with an ultrasound transducer element, a sonication grid density or a time interval between consecutive series of sonications for causing the disruption of the vascular tissue.

16. The method of claim 15, wherein the sonication grid density is determined based on at least one of the imaging data or an acoustic signal from the target volume.

17. The method of claim 1, wherein the radiation treatment plan comprises at least one of a radiation dose, a direction of an ionizing beam, or activation of at least one radiation generator.

18. A system for enhancing radiation treatment of target tissue, the system comprising:
an imager for acquiring a 3D set of voxels corresponding to a target volume of the target tissue;
an ultrasound transducer for generating and delivering at least one sonication of focused beams confined to the target volume for causing disruption of vascular tissue therein so as to define the target volume;
a controller configured for:
causing the imager to continuously monitor the disruption of vascular tissue in real-time;
based at least in part on the monitored disruption of the vascular tissue, adjusting a sonication parameter value associated with the ultrasound transducer; and
determining, based at least in part on the disruption of the vascular tissue, a radiation treatment plan having a reduced radiation dose for treating the target tissue; and
a radiation treatment system for transmitting the reduced radiation dose to the target volume,
wherein the radiation treatment system transmits the reduced radiation dose to the target volume only if the monitored disruption of vascular tissue substantially matches a desired vascular disruption map.

19. The system of claim 18, wherein the controller is further configured to cause the ultrasound transducer to generate a plurality of sonications, each delivering focused acoustic energy beams to a focal zone in the target volume, and a plurality of the focal zones collectively covers the target volume.

20. The system of claim 19, wherein at least one of the plurality of sonications causes cavitation of microbubbles in the target volume.

21. The system of claim 18, wherein the controller is further configured to define a center region and a peripheral region of the target volume, a first intensity of the focused acoustic energy beams in the center region being different from a second intensity of the focused acoustic energy beams in the peripheral region.

22. The system of claim 21, wherein the first intensity is larger than the second intensity.

23. The system of claim 18, wherein the controller is further configured to:
identify a radiation-sensitive region outside the target volume; and
define a first region and a second region of the target volume, the first region being closer to the radiation-sensitive region than the second region to the radiation-sensitive region,
wherein a first intensity of the focused acoustic energy beams in the first region is larger than a second intensity of the focused acoustic energy beams in the second region.

24. The system of claim 18, further comprising an administration device for locally or systemically injecting microbubbles into the target volume.

25. The system of claim 18, wherein the controller is further configured to generate a vascular disruption map of the target volume.

26. The system of claim 25, wherein the vascular disruption map is generated based on at least one of MRI perfusion imaging, MRI contrast imaging, a planning map of vascular disruption, or an acoustic response of the target volume during disruption of the vascular tissue.

27. A system for enhancing radiation treatment of target tissue, the system comprising:
an imaging device for acquiring a 3D set of voxels corresponding to a target volume of the target tissue;
an ultrasound transducer for generating and delivering at least one sonication of focused beams confined to the target volume for causing disruption of vascular tissue therein so as to define the target volume;
a controller configured to:
generate a vascular disruption map of the target volume;
compare a target volume in the vascular disruption map to the 3D set of voxels associated with the target volume acquired by the imaging device; and
determine, based at least in part on the disruption of the vascular tissue, a radiation treatment plan having a reduced radiation dose for treating the target tissue; and
a radiation device for transmitting the reduced radiation dose to the target volume,
wherein the target volume is exposed to the reduced radiation dose only if the target volume in the vascular disruption map substantially matches the target volume acquired by the imaging device.

28. The system of claim 25, wherein the vascular disruption map includes disruption levels of tissue in the target volume.

29. The system of claim 28, wherein the controller is further configured to determine the radiation treatment plan based on the disruption levels.

30. The system of claim 18, wherein the imaging device further acquires a plurality of images for continuously tracking the target volume defined by the disruption of vascular tissue; and the controller is further configured to adjust the radiation treatment plan to compensate for movement of the target volume.

31. The system of claim 18, wherein the controller is further configured to generate a sonication plan comprising at least one of an intensity, a phase, or a frequency associated with an ultrasound transducer element so as to generate and deliver the at least one sonication of focused beams.

32. The system of claim 18, wherein the controller is further configured to:

generate a sonication plan comprising at least one of a sonication grid density or a time interval between consecutive series of sonications; and based on the sonication plan, cause the ultrasound transducer to generate a plurality of sonications for causing the disruption of the vascular tissue.

33. The system of claim 32, wherein the controller is further configured to determine the sonication grid density based on at least one of the imaging data or an acoustic signal from the target volume.

34. The system of claim 18, wherein the radiation treatment plan comprises at least one of a radiation dose, a direction of an ionizing beam, or activation of at least one radiation generator.

* * * * *